(12) United States Patent
Krausa et al.

(10) Patent No.: US 6,521,119 B2
(45) Date of Patent: Feb. 18, 2003

(54) METHOD AND DEVICE FOR THE DETECTION OF NOT EASILY VOLATIZED SUBSTANCES

(75) Inventors: Michael Krausa, Pfinztal (DE); Klaus Schorb, Rheinstetten (DE); Stefan Krebs, Karlsruhe (DE); Frank Becker, Karlsruhe (DE)

(73) Assignee: Fraunhofer-Gesellschaft zur Forderung der angewandten Forschung e.V., München (DE)

( * ) Notice: Subject to any disclaimer, the term of this patent is extended or adjusted under 35 U.S.C. 154(b) by 0 days.

(21) Appl. No.: 09/824,704

(22) Filed: Apr. 4, 2001

(65) Prior Publication Data

US 2001/0027927 A1 Oct. 11, 2001

Related U.S. Application Data

(63) Continuation of application No. 09/177,616, filed on Oct. 23, 1998, now abandoned.

(30) Foreign Application Priority Data

Oct. 31, 1997 (DE) .......................................... 197 48 124

(51) Int. Cl.⁷ .............................................. G01N 27/26
(52) U.S. Cl. .................... 205/780.5; 204/400; 204/434; 204/412; 205/775; 205/787
(58) Field of Search ................................ 204/434, 400; 205/775, 780.5, 787

(56) References Cited

U.S. PATENT DOCUMENTS 4,146,437 A  *  3/1979  O'Keefe
5,597,473 A  *  1/1997  Hambitzer et al.

* cited by examiner

*Primary Examiner*—T. Tung
(74) *Attorney, Agent, or Firm*—Paul Vincent

(57) ABSTRACT

A method and device for the detection of substances such as nitrotoluene, trinitrotoluene, dinitrotoluene, or derivatives, wherein a working electrode and an opposing electrode are contacted with the substance via a viscous electrolyte layer and a voltage is applied to the working electrode whose value is increased and decreased at least once with substantially equal beginning and end values within a predetermined time period, wherein the current strength is determined during this at least one measurement cycle in dependence on the applied voltage, is distinguished in that a plurality of measurement cycles are scanned, and differences of current values of sequential measurement cycles are determined and, in the event of the occurrence of a cathode current maximum, the associated voltage value is determined, held constant and the current strength extracted.

28 Claims, 6 Drawing Sheets

METHOD AND DEVICE FOR THE DETECTION OF NOT EASILY VOLATIZED SUBSTANCES

This application is a continuation of application Ser. No. 09/177,616 filed Oct. 23, 1998 now abandoned and claims Paris Convention Priority of German patent application number 197 48 124.8 filed Oct. 31, 1997, wherein the complete disclosure of both are hereby incorporated by reference.

BACKGROUND OF THE INVENTION

The invention concerns a method for the detection of not easily volatized substances, in particular of Nitrotoluene, trinitrotoluene, dinitrotoluene or derivatives of nitrotoluene as well as chemical warfare materials such as Clark, Lewisite, Lost, Sarin, Soman, Tabun or the like in soil, liquids and gases, wherein an electrode configuration having at least one working electrode and an opposing electrode is brought into contact with the substance to be examined via an electrolyte and a voltage is applied to the working electrode whose value is increased and decreased within a predetermined measuring time at least once and having the substantially same beginning and end values, wherein the strength of the current during this at least one measurement cycle is determined in dependence on the applied voltage. The invention also concerns a device for the detection of not easily volatized substances, in particular of nitrotoluene, trinitrotoluene, dinitrotoluene or derivatives of nitrotoluenes as well as of chemical warfare materials such as Clark, Lewisite, Lost, Sarin, Soman, Tabun or the like in soil, liquids and gases having a sensor element comprising at least one working and one opposing electrode which are connected to a regulated voltage source and which come in contact with an electrolyte.

Potentiostatic (amperometric) measuring systems are usually used, e.g. to detect gaseous substances which are not easily volatized, wherein a potential is applied to a substantially porous, large electrode. Electrochemical oxidation or reduction leads to the quantitative detection of the substance present via the amount of current flow. The qualitative detection is thereby preferentially facilitated by gas chromatography or by high pressure liquid chromatography (HPLC) or other methods with which the mentioned electrochemical systems are utilized as detectors.

In the conventional electrochemical sensor systems for gas phase analysis, which can also be based on semiconductor technology, the electrodes are separated from the gas volume by means of a membrane or polymer layer, wherein the substance to be detected diffuses through a permeable membrane and is subsequently dissolved in the internal electrolytes which are in contact with the electrodes. The detection of the respective substance is thereby effected by means of electrochemical oxidation or reduction at the working electrode. As has already been mentioned, a fixed potential is applied to the working electrode.

These types of methods, e.g. gas chromatography, have the disadvantage of being time consuming and expensive. In the event that liquids or soil is investigated it is first necessary to collect samples and remove same to a predetermined analysis location.

In addition, most explosive charges are produced using trinitrotoluene (TNT) or with the addition of TNT for reasons of simplicity of production and processing. Since this type of explosive is also used for extortion or terrorist threats as well as attacks, the detection of this type of explosive, e.g. during luggage and passenger checks for air travel, is an important task in order to prevent danger to human life. Also when searching for plastic encased mines, rapid and uncomplicated detection is imperative. TNT utilized for explosive charges or for the production of mines is a solid which releases small amounts of vapor to the surrounding environment.

In order to detect this type of contamination in soil, liquids and gases, EP-A-O 665 431 has already proposed a device working on the basis of cyclic voltammetry. This device has a sensor element comprising three electrodes, a working electrode, a reference electrode as well as an opposing electrode and having a regulated voltage source. A voltage is applied to the working electrode, the cyclic reduction and increase of which accompanied by simultaneous measurement of the current flow in dependence on the applied voltage, produces so-called voltammograms, obtained in the form of voltage-current curves. The voltage values on the respective working electrodes during the occurrence of cathode or anode current peaks for reduction and oxidation of the redox pairs represent a quantitative measurement for the contamination present. The quotient between the current strength of the anode current maximum and the measured current in the so-called double layer region leads to the determination of the TNT content. The above mentioned device can determine the TNT content or that of other substances per se, however the sensitivity is insufficient in the event of very small vapor pressures. In particular, a determination of substances in the gas phase is not possible with this device, since the determination of gas phase substances requires use of a membrane by means of which a flow-through cell is separated from the electrolyte solution.

It is therefore the underlying purpose of the invention to further improve a method as well as a device of the above mentioned kind in such a fashion that electrochemically reactive substances can be detected even in very small concentrations and/or vapor pressures and in a qualitatively as well as a quantitatively reliable manner.

SUMMARY OF THE INVENTION

This purpose is achieved in accordance with the invention by means of a method of the above mentioned kind in that a plurality of measurement cycles are carried out and the differences of current strengths of sequential measurement cycles are determined and, in the event that a cathode peak maximum occurs, the associated voltage value is determined, held constant and the current strength is determined. A device in accordance with the invention is distinguished in that the electrolyte is applied in the form of a thin layer onto the end surface of a sensor element coming in contact with the substance under investigation.

It has turned out that the cyclic voltammogram, for a plurality of cycles of the measurement cycle, stabilizes itself in such a fashion that reduction leads to a characteristic maximum (cathode current peak). Determination of the difference of the measured current values allows the occurrence of such a characteristic maximum to be determined in an optimal and rapid fashion. In accordance with the invention, when a cathode current peak occurs, the associated voltage value is determined, held constant and the current strength is then determined in a potentiostatic manner over time up to saturation. In this manner, the sensitivity is increased and the time for detection reduced. The qualitative detection is done by means of the peak potential determination and the quantitative detection by means of the potentiostatic measurement of the current height. In this manner, the response time is substantially improved. For example, response times of less than 0.5 seconds can be achieved.

The device in accordance with the invention provides that the requisite electrolyte be applied in the form of a thin layer on the end of the sensor element and not, as was conventional, by submerging the sensor element into an electrolyte. The thickness of the electrolyte layer influences the detection time. The method as well as the device in accordance with the invention thereby facilitate reliable detection of the most differing of not easily volatized substances even in small concentrations. The optimal achievable potential value with which a cathode current peak (negative sign) occurs is approached in a stepwise fashion using the method in accordance with the invention.

In order to prevent the measuring time from increasing unnecessarily, one measurement cycle spans, at most, the potential region between hydrogen and oxygen development.

The extracted or determined values with respect to current height, differences and potential can be output optically or acoustically. For example, an acoustical signal can change in dependence on the determined concentration of the respective substance. This is particularly advantageous when approaching a mine due to the associated increased concentration of TNT.

If the measuring medium, under all conditions, remains constant during passage through the measuring cycle, this leads to no change in the potential of the opposing or of a reference electrode respectively, when the latter is utilized. The potential associated with the cathode current maximum can correspondingly be used for detection of the subsequent TNT reduction. If however the measuring medium changes or the electrolyte composition changes with time this leads to a displacement of the potential. For this reason, instead of using the absolute potential at the cathode current maximum to determine the substance, a further improvement provides for use of the potential difference of the voltage values or potentials between an anode current maximum signifying an oxygen reduction and the cathode current maximum. It has been shown that this potential difference between the cathode current maximum and the oxygen reduction peak remains constant for the corresponding substance over a plurality of measurements. Measurements have shown that for 2.4-TNT and 2.6-TNT, a difference of approximate 840 mV is present. There is solely a dependence on the corresponding solvent and on the electrolyte utilized. 3.4-TNT has a different quantity of 950 mV. For 2-amino-5-nitrotoluene, measurements have revealed two reduction peaks of which one peak has a difference with respect to the oxygen reduction peak of approximately 860 mV and a second a difference of 480 mV. Knowledge of these potential differences thereby simplifies detection of the corresponding substance.

On order to perform continuous measurements, a substance under investigation is passed by the sensor element having the working electrode. In the event of a gas phase substance, this is preferentially passed through a flow-through cell. The gas phase substance is thereby preferentially pumped through the flow-through cell and passed by the sensor element. In this manner, even substances of low concentration and low equilibrium vapor pressure can be detected.

In order to be able to apply the electrolyte to the sensor elements in a simple and rapid fashion, same is preferentially a viscous fluid or a gel-like substance. Such an electrolyte can be applied rapidly and bonds in a reliable fashion to the end of the sensor element. Such a sensor element can also be introduced into a gas volume in a simple and rapid fashion to detect gaseous substances. Membranes are no longer needed to separate the gas volume from the electrolyte.

Electrolytes can, in addition to inorganic compounds (sulfuric acid, perchloric acid among others), also be mixtures made from inorganic and organic compounds (acetone/acid, ethanol/sulfuric acid, hexane-1-sulphonate/sulfuric acid among others) as well as pure organic compounds (acetone, ethanol among others). The choice of the respective electrolyte depends on the required sensitivity and selectivity when carrying out the method in accordance with the invention and therefore can be tailored to the substance to be detected.

A preferred embodiment provides that at least the working and/or opposing electrodes are microelectrodes. Preferentially they are ultra microelectrodes. In this manner, the measurement can be carried out with a simple two electrode configuration. The opposing electrode is simultaneously the reference electrode. This simple construction is possible since the potential on the opposing electrode remains nearly constant throughout the measuring cycle in consequence of the low current flowing at the microelectrodes.

The working electrode is preferentially substantially enclosed in a ring-shaped fashion by the opposing electrode. In this manner, a compact construction of the sensor element is nevertheless associated with a large surface for the opposing electrode as well as an even current distribution on the working electrode. In addition, the opposing electrode is thereby substantially non-polarizable in the electrolyte, since the surface of the opposing electrode in contact with the electrolyte is substantially larger than that of the working electrode.

The sensor elements can also be equipped with a plurality of working electrodes and/or a separate reference electrode can also be incorporated.

An improvement provides that electrodes be disposed insulated from each other within a measuring head. The electrolyte layer is then introduced on the lower side or end of the measuring head. The measuring head is preferentially made from glass or from a mould substance such as ARALDITE or the like. These substances could also serve as insulators between the electrodes.

The triangular shaped voltage/time dependence in cyclic voltammetry at the working electrode facilitates, in addition to the quantitative and quantitative information, additional monitoring of the surface of the sensor element or of the measuring head as well as self-calibration of the system.

An improvement provides that a flow-through probe be disposed below the sensor element or the measuring head. In this manner, gaseous substances can be easily continuously investigated. For example, the flow through cell can be bolted onto the sensor element. In this manner, the substances to be detected can be selectively and reliably measured. Improvements provide for a seal between the measuring head and the flow-through cell. A pumping device is preferentially provided in order to guide the gas past the measuring head. The membrane of prior art is no longer necessary in the device in accordance with the invention to analyze gaseous substances.

A further preferred configuration provides that the sensor element or the measuring head can be connected to a regulation and evaluation electronics. In this manner, the current values measured at the applied voltage values, the voltage values, and the differences of the current values can be analyzed and the corresponding concentrations of the material to be detected can then be indicated. An output unit to display concentrations is preferred so that same can be directly read during measurement. It is also possible to indicate the values not only optically but also acoustically, wherein e.g. an alarm unit for output of an alarm signal, in the event that a predetermined concentration is exceeded, can be provided for, wherein the acoustical signal can advantageously depend upon the concentration.

The method in accordance with the invention and the device in accordance with the invention thereby allow for the qualitative and quantitative detection of electrochemically reacting substances even at very small vapor pressures. The use of differing electrode materials and electrolytes in the measuring head or the sensor element can provide for a selective detection of differing substances. The sensitivity and selectivity of the measurement system which thereby result allow for applications in the most differing of regions, e.g. environmental protection as well as personnel protection in which the polluting chemical substances must be detected in low concentrations. For example, TNT can thereby be detected in the gaseous phase. In addition, the method and the device in accordance with the invention can be utilized not only e.g. to search for mines containing TNT but also for explosive charges and for the cleaning of contaminated surfaces in a reliable and rapid manner. In addition, a series of other substances e.g. chemical weapons such as Sarin, Clark I, Lewisite, Soman, Tabun as well as Lost etc. and drugs and substances having high vapor pressures can be detected.

Further advantages and features of the invention can be extracted from the claims and the subsequent description in which an embodiment is described in detail with reference to the drawing.

DESCRIPTION OF THE PREFERRED EMBODIMENT

Figure 1:
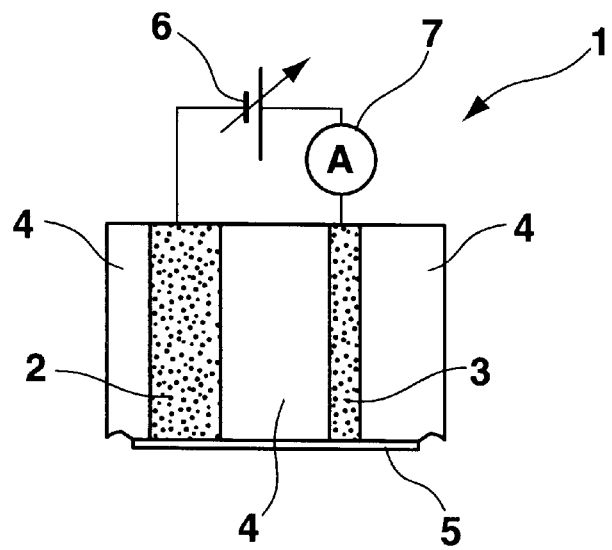
FIG. 1 shows a schematic representation of a measuring head of the device in accordance with the invention in a longitudinal cut.

A sensor element or a measurement head 1 shown in FIG. 1 has, in the embodiment shown, an opposing and reference electrode 2 as well as a working electrode 3. The working electrode 3 has a smaller diameter that the opposing and reference electrode 2 and is separated and insulated therefrom by means of an insulator 4 surrounding both electrodes as well as the intermediate space. A viscous or gel electrolyte film 5 is introduced on the end of the measuring head. Its contact surface with the opposing and reference electrode 2 is, due to its diameter, substantially larger than that of the working electrode 3. In this manner, the opposing and reference electrode 2 is substantially non-polarizable so that only two electrodes are required in the measuring head in this constellation. In this manner, the opposing electrode 2 assumes the function of the reference electrode. The opposing and reference electrode 2 as well as the working electrode 3 are connected to a common voltage source 6 whose voltage can be regulated in a variable manner. In addition, amperometer 7 is provided for measurement of the current strength.

Figure 2:
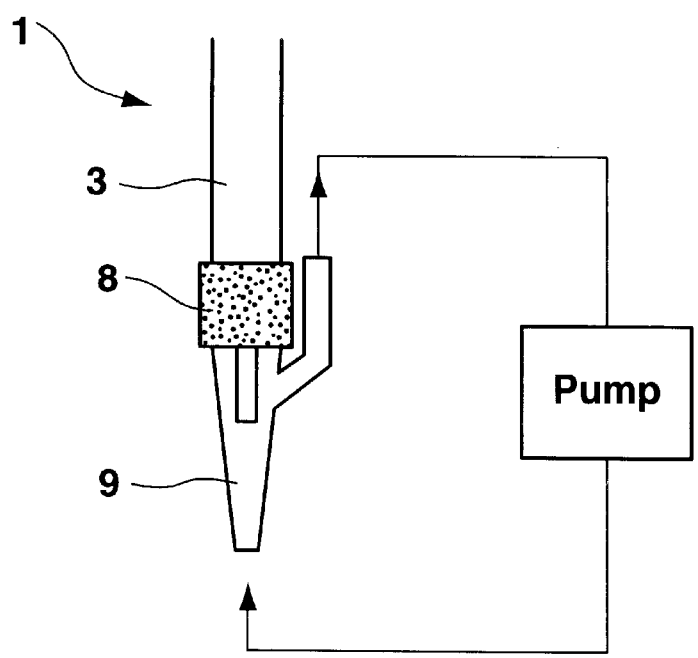
FIG. 2 shows the configuration of a measuring head in accordance with the invention above a flow through cell for gases.

In the embodiment shown in FIG. 2, the sensor element 1 is disposed with its working electrode 3 above a flow-through measuring cell 9 through which a gas containing the substance to be detected is pumped via a pump (not shown) in the direction corresponding to the arrow. A seal 8 is thereby provided between the measurement cell 9 and the electrode 3. The substance gains direct access to the electrode layer 5 without having to diffuse through an intermediate membrane.

Figure 3A:
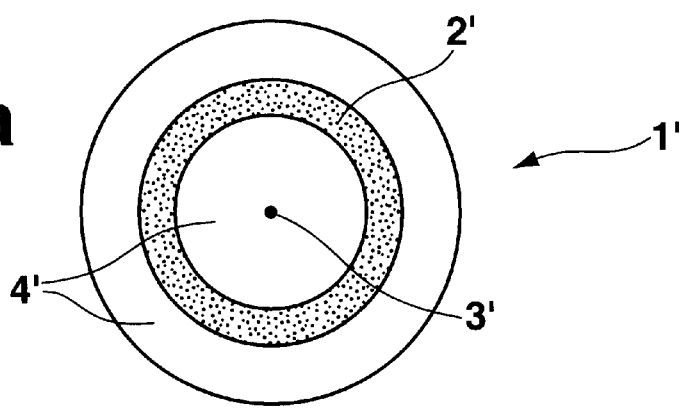
FIG. 3a shows a cross section through a first embodiment of a measuring head in accordance with the invention.
Figure 3B:
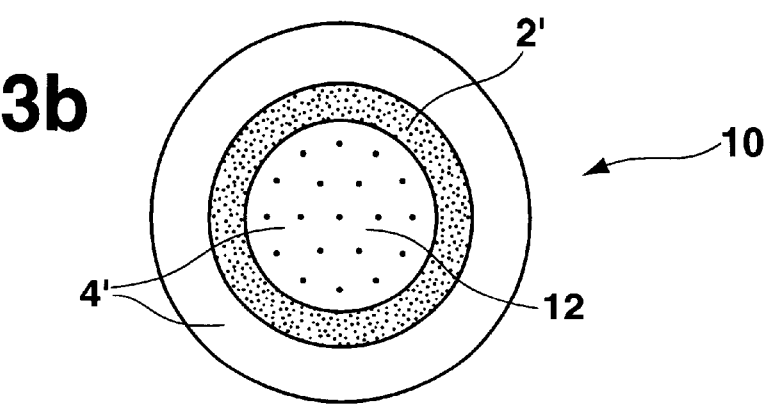
FIG. 3b shows a cross section through a second measuring head in accordance with the invention.
Figure 3C:
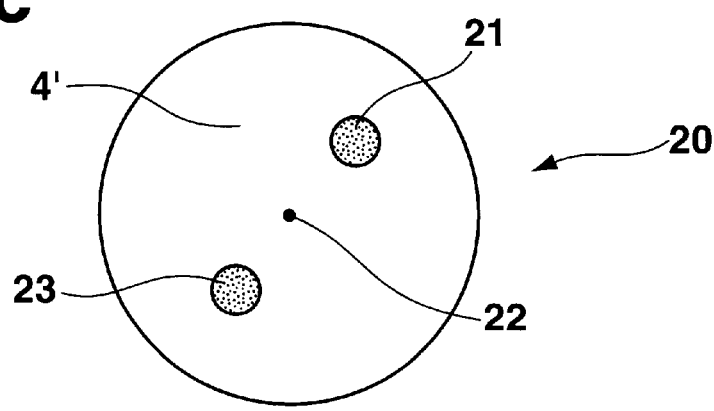
FIG. 3c shows a cross section through a third measuring head in accordance with the invention.

In the embodiment shown in FIGS. 3a through 3c, differing configurations and embodiments of opposing, reference and working electrodes are illustrated. In the embodiment shown in FIG. 3a, the opposing electrode 2', which also serves as the reference electrode, is ring-shaped and completely surrounds the pin-shaped working electrode 3'. In the embodiment shown in FIG. 3b, a plurality of working electrodes 12 are disposed within the ring-shaped opposing/reference electrode 2'. In the embodiment shown in FIG. 3c, the working electrode 22 is disposed between the opposing electrode 23 and a separate reference electrode 21 within the insulator 4' of the measuring head 20. This type of insulator 4' is clearly also provided for in the measuring head 10 of FIG. 3b as well as in the measuring head 1' of FIG. 3a.

Figure 4:
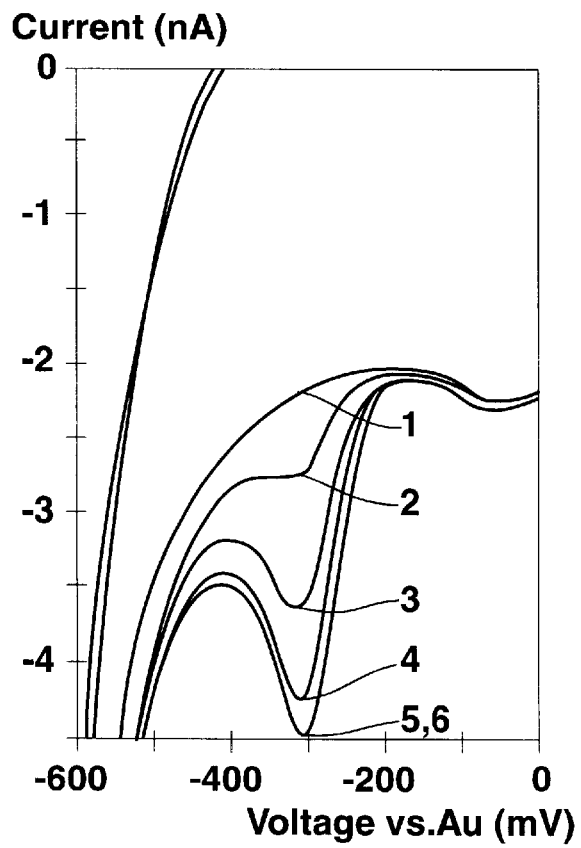
FIG. 4 shows a current-voltage curve of a trinitrotoluene (TNT) sample having six cyclic repetitions.
Figure 5:
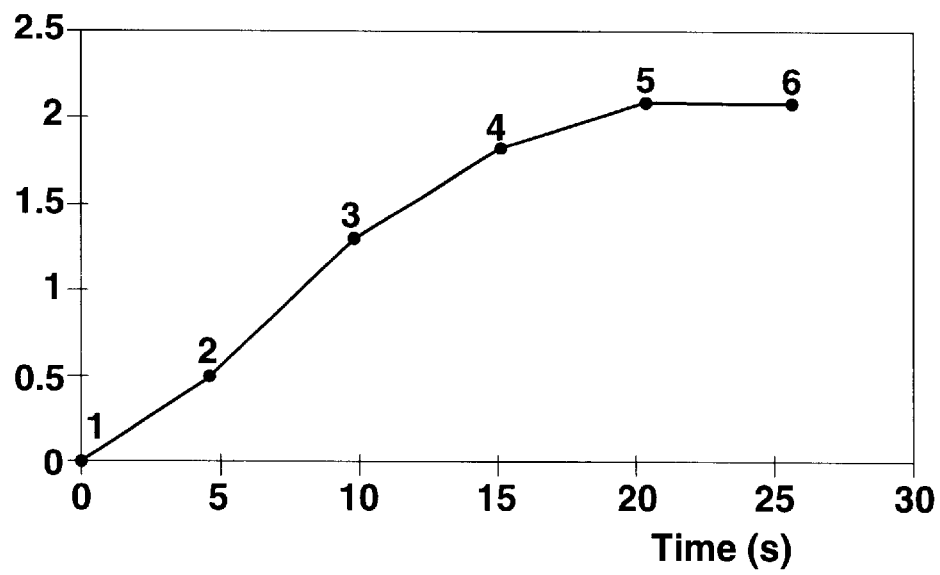
FIG. 5 shows the cathode current peaks plotted against the measurement time from FIG. 4 as a function of the cycle number.
Figure 6:
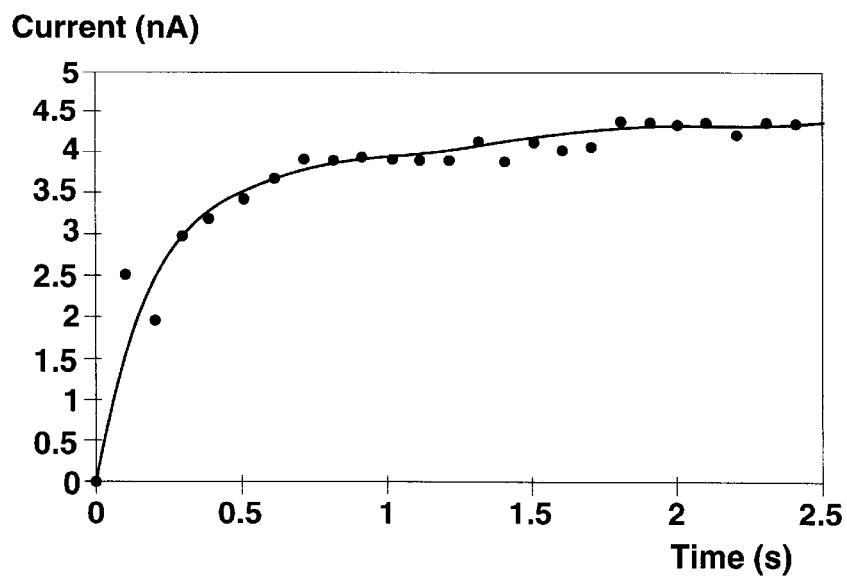
FIG. 6 shows the current curve of the current values determined at the cathode current maximum in FIG. 4 at constant voltage.

FIG. 4 shows the current-voltage curve for a TNT sample having six cyclic repetitions in the vicinity of the cathode current peak at −300 mV. As the six differing measuring curves show, there is no typical current peak at the beginning of the first measurement cycle 1. This begins to form slightly during the second measurement cycle which can be seen in curve 2 of FIG. 4. In this potential region in the vicinity of −300 mV, the TNT content in the sample is reduced. In the subsequent additional measurement cycles 3 through 6, this cathode current peak becomes increasingly prominent, wherein the last two curves 5 and 6 are identical. This development of the cathode current peak can also be extracted from FIG. 5. The dependence of these current peaks at −300 mV thereby allows determination of a cathode current peak. The potential sweep is thereby fixed at −300 mV and the current heights as shown in FIG. 6 are then determined in dependence on the measuring time at fixed voltage. As can be seen in FIG. 6, a nearly constant current value already occurs under these potentiostatic conditions after a response time of 0.5 seconds. By means of this current value, the concentration of TNT can be determined and output with the current values thereby remaining substantially unchanged.

The thickness of the electrolyte layer can influence the detection time so that, e.g. in the event of a thicker film, a constant current value first occurs with constant potential after 40 seconds.

The combination of a potentiodynamic and potentiostatic measurement permits a reliable detection of the substances under investigation. The measurement effects potential sweeps until a current peak of a corresponding substance to be detected occurs. At this location, as can be seen from FIGS. 4 through 6, the potential sweep is stopped and pure potentiostatic measurements of the change of the current versus time are then recorded.

Figure 7:
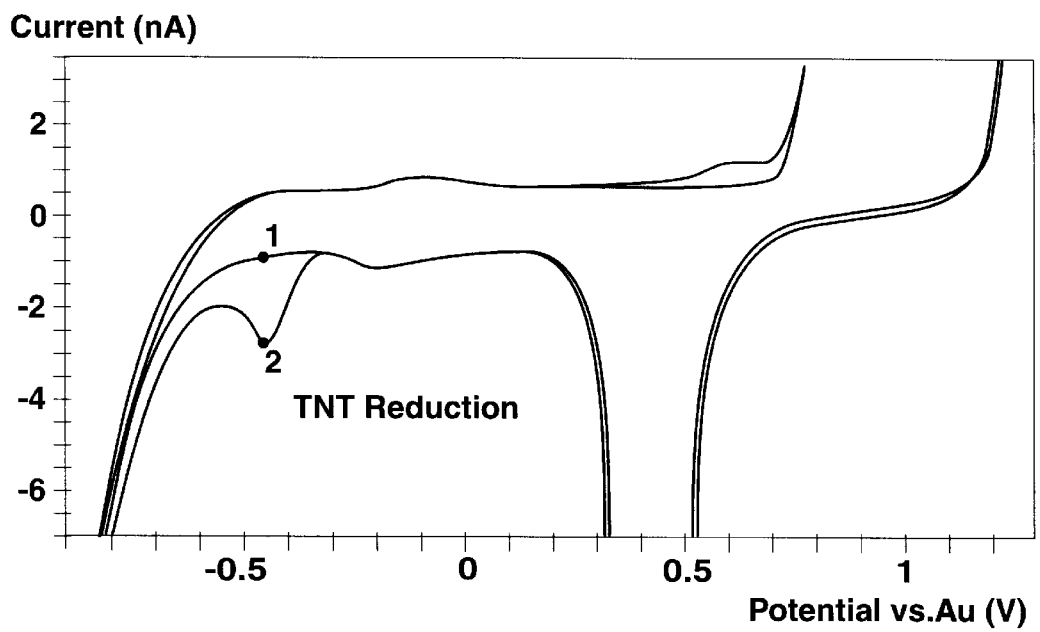
FIG. 7 shows a voltage-current curve for trinitrotoluene (TNT) with hexane-1-sulphonate in sulfuric acid as electrolyte.

In a concrete embodiment of the method in accordance with the invention, the current-voltage curve for TNT, which has a vacuum pressure of 0.057 mbar at 81° C., is recorded at 20° C. Hexane-1-sulphonate in sulfuric acid is utilized as electrolyte and the working electrode is gold. The potential or the voltage of the working electrode is varied relative to the potential of the reference electrode with a triangular dependence over time to extract a cyclic voltammogram. The current-voltage curve for this particular example is shown in FIG. 7.

The potential range during taking of these curves is between −600 mV and −250 mV. In this region, the dependence of the curve for the establishment of a cathode current peak (negative sign) is evaluated. As the two differing measuring curves 1 and 2 in FIG. 7 show, no typical current peak is recognizable at the beginning of the first measurement cycle 1. This first occurs after passage of a plurality of measurement cycles as represented in curve 2. In this potential region, TNT is typically reduced. The associated potential value thereby provides qualitative information concerning the presence of TNT and the current height, quantitative information concerning the concentration. In order to then determine whether such a cathode current peak is present, the differences of the current values of sequential measurement cycles are determined and can be output optically or acoustically. If, as can be seen from FIG. 7, a cathode current peak occurs in the potential region, the potential sweep is stopped at this potential and the current height is measured subsequently at constant potential or constant voltage as shown in FIG. 6 for another sample.

Figure 8:
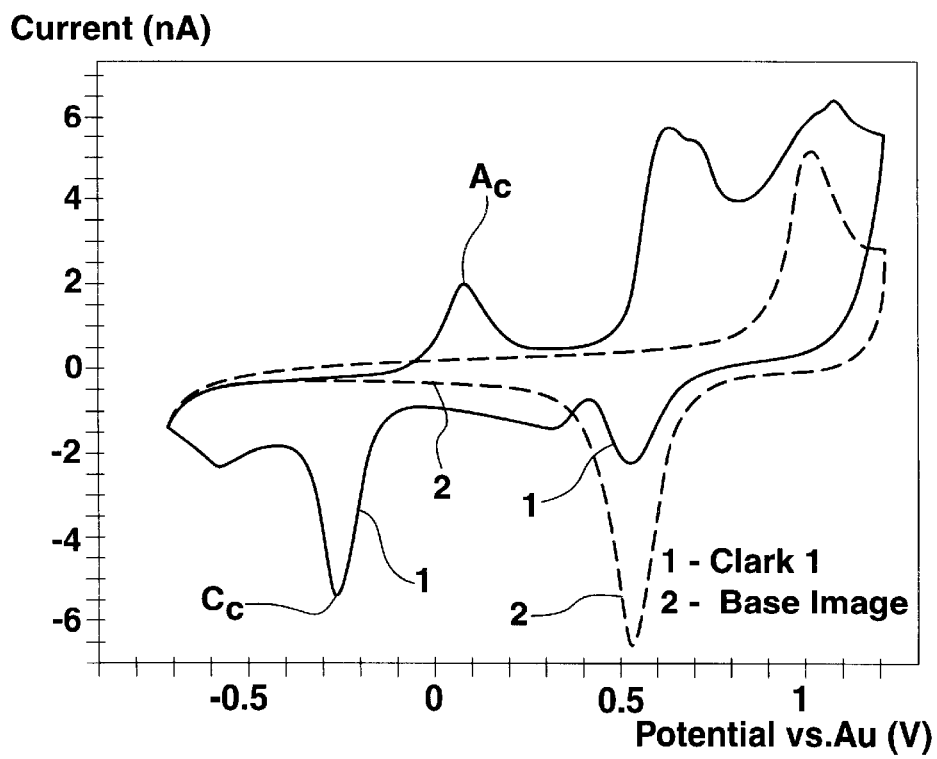
FIG. 8 shows current voltage curves for Clark I using a gold electrode.
Figure 9:
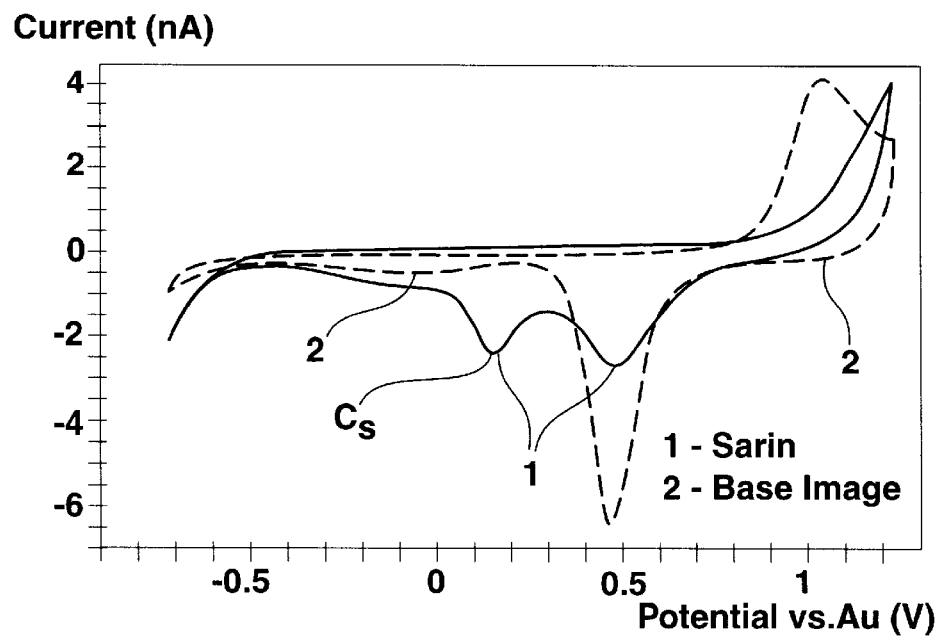
FIG. 9 shows current voltage curves for Sarin using a gold electrode.
Figure 10:
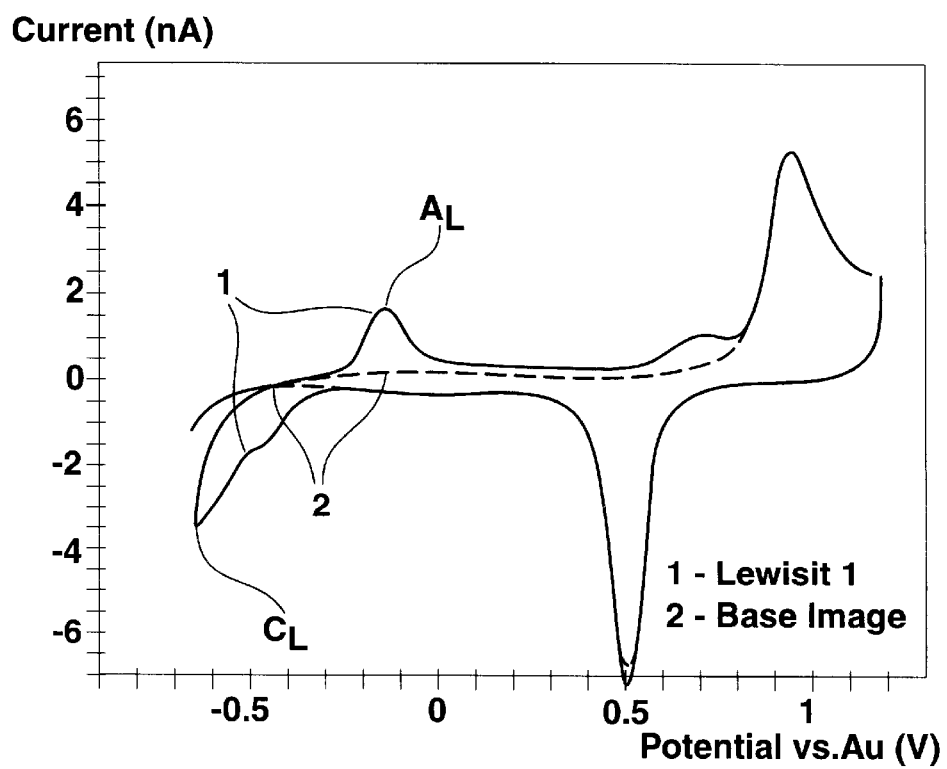
FIG. 10 shows current voltage curves for Lewisite using a gold electrode.

FIGS. 8 through 10 show three additional current-voltage curves for differing chemical warfare substances, namely Clark 1 (FIG. 8), Sarin (FIG. 9) and Lewisite I (FIG. 10). A gold electrode is used as a working electrode. The potential or the voltage of the working electrode is then likewise varied in a triangular manner over time relative to the potential of the reference electrode to obtain a cyclic voltammogram.

The potential region spanned during recording of these current-voltage curves lies between −700 mV and 1200 mV. In this region, the dependence of the curves, in each case, on the build-up of a cathode current peak (negative sign), is evaluated. As the base images 2 at the beginning of each measurement in FIGS. 8 through 10 show, no substance-typical current peak can be extracted from the first current-voltage curve 2.

These establish themselves only after a plurality of swept measurement cycles as is represented in the corresponding current-voltage curve 1 in FIGS. 8 through 10.

In the event that one is dealing with the chemical weapon Clark I, the current-voltage curve 1 shows a substance-specific cathode current peak $C_c$ after a plurality of measurement cycles at approximately −250 mV. If one is dealing with Sarin (FIG. 9), the current-voltage curve 1 displays a substance-specific cathode current peak at $C_s$ approximately 150 mV. The current-voltage curve for determining Lewisite I (FIG. 10) has a cathode current peak $C_L$ in the vicinity of approximately −600 mV. These three chemical warfare materials are typically reduced in these potential regions. Associated potential values thereby provide qualitative information concerning the presence of these three chemical weapons, whereas the current heights facilitate quantitative information concerning the concentration. The subsequent procedure is equivalent to that already described with reference to FIGS. 4 through 7.

As further shown in FIGS. 8 and 10, the current-voltage curves for Clark 1 as well as for Lewisite I also display anode maxima $A_c$, in the vicinity of 100 mV for Clark I, and $A_L$ in the range of −150 mV for Lewisite I. These substance-specific anode current maxima, which represent oxidation of the substance to be determined, can also be utilized for detection, if appropriate.

We claim:

1. A method for the detection of a not easily volatized substance such as nitrotoluene, trinitrotoluene, dinitrotoluene and derivatives of nitrotoluenes as well as chemical warfare materials such as Clark, Lewisite, Lost, Sarin, Soman, Tabun and the like in soil, liquid and gas, the method comprising the steps of:

a) applying a viscous electrolyte layer to an electrode configuration, said electrode configuration comprising at least a working electrode and an opposing electrode, said viscous electrolyte applied to completely cover said working electrode and said opposing electrode;

b) bringing the substance into contact with said electrode configuration such that the substance only contacts said working electrode and said opposing electrode via said viscous electrolyte layer;

c) applying a voltage to said working electrode;

d) increasing said voltage and decreasing said voltage in a first measuring cycle between substantially equal beginning and ending voltage values and within a predetermined period;

e) determining cathodic current values occurring during step d) in dependence on said increasing and decreasing voltage;

f) extracting at least one cathodic current maximum at at least one associated first voltage;

g) keeping said first voltage of step f) constant and successively determining associated cathodic current strengths as a function of time at said constant first voltage until said cathodic currents strengths remain substantially unchanged; and h) determining a substance concentration from said substantially unchanged cathodic current strengths.

2. The method of claim 1, wherein a voltage range spanned in step d) does not exceed a potential region between hydrogen and oxygen development.

3. The method of claim 1, further comprising the step of optically outputting said first voltage and associated current strengths of step g).

4. The method of claim 1, further comprising the step of acoustically outputting said first voltage and current strengths of step g).

5. The method of claim 1, further comprising the steps of determining a second voltage associated with an anode current maximum indicating oxygen reduction and extracting a potential difference between said first voltage and said second voltage.

6. The method of claim 1, further comprising passing the substance by said electrode configuration.

7. The method of claim 6, wherein the substance is a gas passed by said electrode configuration by pumping through a flow-through cell.

8. The method of claim 1, further comprising the steps of applying said voltage to said working electrode, decreasing said voltage, and increasing said voltage in steps c) and d) using voltage application means having a regulated voltage source connected to said working electrode and said opposing electrode.

9. The method of claim 8, wherein said electrolyte is a gel.

10. The method of claim 8, further comprising selecting said electrolyte to comprise organic compounds.

11. The method of claim 8, further comprising selecting said electrolyte to consist essentially of inorganic compounds.

12. The method of claim 8, further comprising selecting said electrolyte to consist essentially of a combination of organic and inorganic compounds.

13. The method of claim 8, further comprising selecting said working and said opposing electrode to each consist essentially of a microelectrode.

14. The method of claim 8, further comprising structuring said working electrode to be substantially surrounded in a ring-shaped manner by said opposing electrode.

15. The method of claim 8, further comprising bringing the substance into contact with a plurality of working electrodes.

16. The method of claim 8, further comprising bringing the substance into contact with an additional reference electrode.

17. The method of claim 8, further comprising disposing said working and said opposing electrodes within a measuring head and insulating said working and said opposing electrode from each other.

18. The method of claim 17, further comprising structuring said measuring head from glass.

19. The method of claim 18, further comprising structuring said measuring head from a mould substance.

20. The method of claim 8, further comprising disposing one of a flow-through cell and a measurement cell below said working electrode and said opposing electrode.

21. The method of claim 20, further comprising attaching one of said flow-through cell and said measurement cell to said working electrode and said opposing electrode.

22. The method of claim 21, further comprising disposing a seal member for separation between said electrode configuration and one of said flow-through cell and said measurement cell.

23. The method of claim 20, further comprising pumping the substance through one of said flow-through cell and said measurement cell.

24. The method of claim 8, further comprising connecting a regulation and evaluation electronics to said working electrode and said opposing electrode.

25. The method of claim 8, further comprising displaying a concentration on an output unit.

26. The method of claim 1 further comprising:
   i) repeating steps d) and e);
   j) determining differences of cathodic current values between successive repetitions of steps d) and e); and
   k) repeating steps d) through j) until said differences of cathodic current values are substantially zero.

27. A device for the detection of a not easily volatized substance such as nitrotoluene, trinitrotoluene, dinitrotoluene and derivatives of nitrotoluenes as well as chemical warfare materials such as Clark, Lewisite, Lost, Sarin, Soman, Tabun and the like in soil, liquid and gas, the device comprising:

an electrode configuration having an applied viscous electrolyte layer, said electrode configuration comprising at least a working electrode and an opposing electrode, said viscous electrolyte applied to completely cover said working electrode and said opposing electrode;

means for bringing the substance into contact with said electrode configuration such that the substance only contacts said working electrode and said opposing electrode via said viscous electrolyte layer;

means for applying a voltage to said working electrode;

means for increasing said voltage and decreasing said voltage in a first measuring cycle between substantially equal beginning and ending voltage values and within a predetermined period;

means for determining cathodic current values in dependence on said increasing and decreasing voltage;

means for extracting at least one cathodic current maximum at at least one associated first voltage;

means for keeping said first voltage constant and for successively determining associated cathodic current strengths as a function of time at said constant first voltage until said cathodic currents strengths remain substantially unchanged; and means for determining a substance concentration from said substantially unchanged cathodic current strengths.

28. The device of claim 27 further comprising:
   means for repeating said first measuring cycle; and
   means for determining differences of cathodic current values between successive repetitions of said first measuring cycle until said differences of cathodic current values are substantially zero.

* * * * *